United States Patent [19]
Saito et al.

[11] Patent Number: 4,665,924
[45] Date of Patent: May 19, 1987

[54] ULTRASONIC IMAGING APPARATUS

[75] Inventors: Kazuyoshi Saito, Yaita; Taketoshi Iida, Tochigi; Toshio Shirasaka, Tochigi; Yasuhiko Takemura, Tochigi, all of Japan

[73] Assignee: Tokyo Shibaura Denki Kabushiki Kaisha, Kawasaki, Japan

[21] Appl. No.: 751,143

[22] Filed: Jul. 2, 1985

Related U.S. Application Data

[60] Division of Ser. No. 546,079, Oct. 28, 1983, Pat. No. 4,541,435, which is a continuation of Ser. No. 238,850, Feb. 27, 1981, abandoned.

[30] Foreign Application Priority Data

Feb. 28, 1980 [JP] Japan .................................. 55-24416
Apr. 2, 1984 [JP] Japan .................................. 59-63282

[51] Int. Cl.⁴ .............................................. A61B 10/00
[52] U.S. Cl. ................................ 128/660; 73/631
[58] Field of Search ............................... 128/660-663; 73/631, 675-676

[56] References Cited

U.S. PATENT DOCUMENTS 4,016,862  4/1977  Lancee et al. ........................ 128/660
4,305,296  12/1981 Green et al. ........................... 73/626

Primary Examiner—Kyle L. Howell
Assistant Examiner—Francis J. Jaworski
Attorney, Agent, or Firm—Finnegan, Henderson, Farabow, Garrett & Dunner

[57] ABSTRACT

Ultrasonic imaging apparatus including ultrasonic transducers for emitting acoustic wave beams of various apertures, apparatus for directing two acoustic wave beams of substantially different focussing distances on the same beam direction, circuitry for receiving the reflected waves corresponding to the beam directions, apparatus for modulating the scanning lines corresponding to the beam directions of the reflected acoustic waves, and apparatus for composing the scanning lines corresponding to the two acoustic beams directed on the same beam direction into a single scanning line for display.

7 Claims, 10 Drawing Figures

FIG. 3 *PRIOR ART*
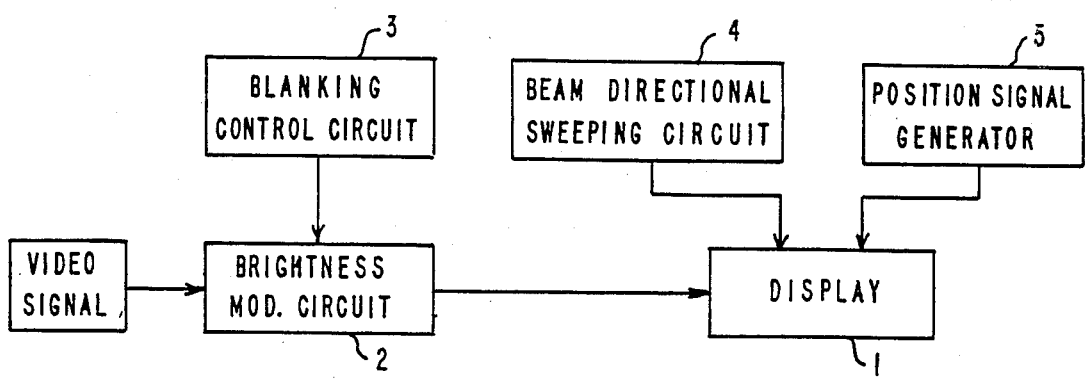
*PRIOR ART* FIG. 4      FIG. 9
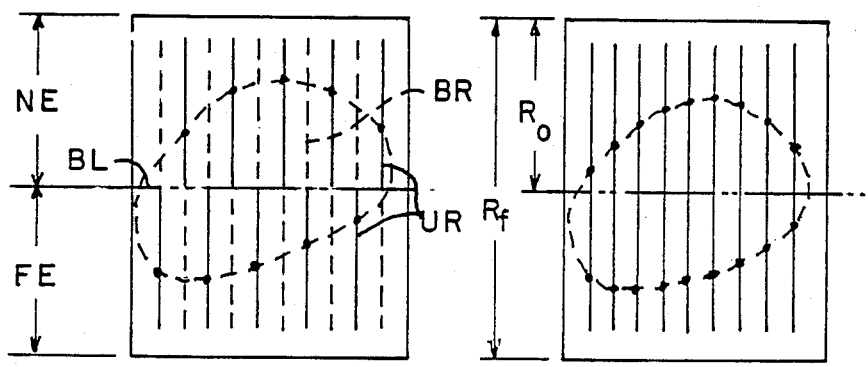
FIG. 5
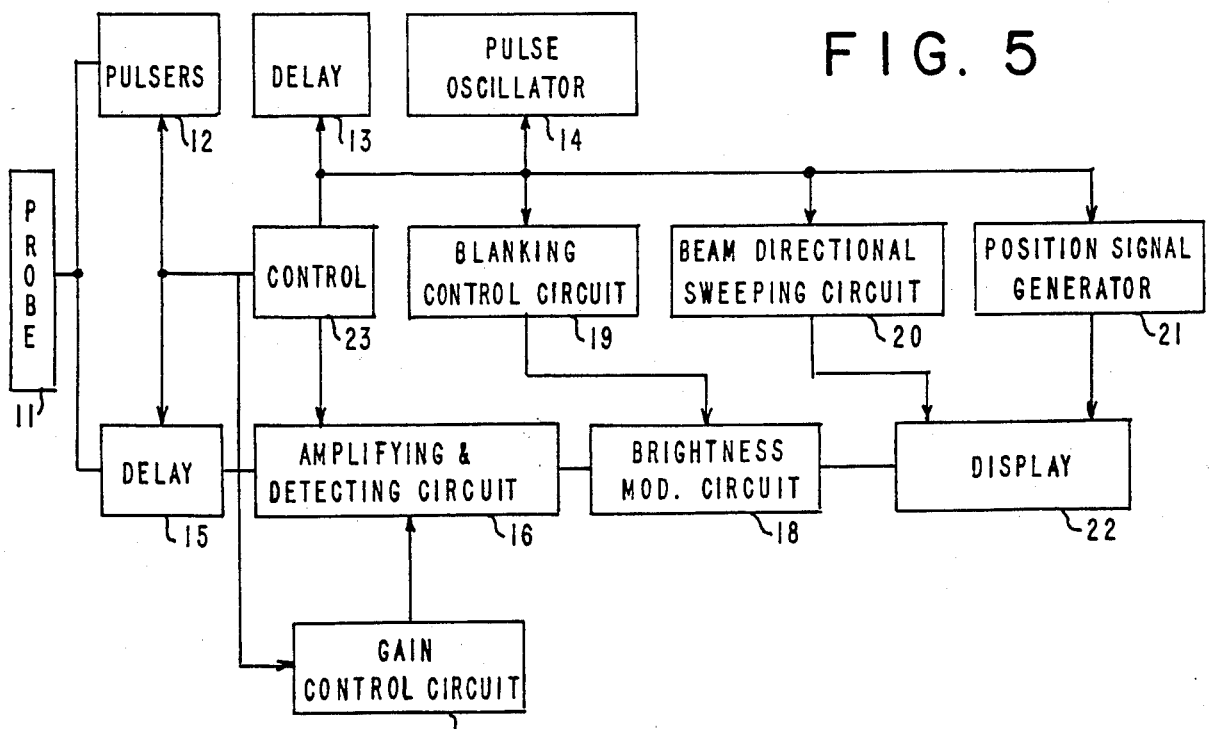

ULTRASONIC IMAGING APPARATUS

This is a division of application Ser. No. 546,079, filed 10/28/83, and now U.S. Pat. No. 4,541,435, which application in turn is a continuation of Ser. No. 238,850 filed 2/27/81 and now abandoned.

BACKGROUND OF THE INVENTION

This invention relates to ultrasonic imaging apparatus and particularly to ultrasonic diagnosis apparatus for forming tomographic images of internal elements of a living body.

In ultrasonic diagnosis apparatus, acoustic beams are emitted into a subject, echoes corresponding to the direction of the beam positions are received, scanning lines corresponding to the beam direction with the echoes are modulated to conform them to a display apparatus, and a tomographic image of the subject is obtained by using the acoustic beams of a plurality of beam directions.

For example, ultrasonic diagnosis apparatus techniques for causing lateral resolution to become more precise include the following:

(i) Apertures of emitted acoustic beams are caused to change corresponding to the required depth being diagnosed, that is, in case the required depth is relatively shallow the beam aperture is caused to be small to improve the lateral resolution. In case the required depth is deep, the beam aperture is caused to be relatively large to provide the scope of the long distance acoustic field, which narrows as it penetrates, and checking deterioration of the lateral resolution because of the extensions of the beams in the long distance acoustic field. Hence, the smaller the beam aperture is, the shallower the scope of the short distance acoustic field is and the larger the beam aperture is, the deeper the scope of the short distance acoustic field is;

(ii). Focusing the emitted acoustic beams causes the lateral resolution to become better defined in the vicinity of the required depth being diagnosed;

(iii). The received beam aperture in echo-receiving time is caused to be small in case of the short distance acoustic field and to be large in case of the long distance acoustic field to define the lateral resolution, more precisely, and;

(iv). The received focusing point in echo-receiving time is caused to shift corresponding to the reflective point of the received echo to provide precise lateral resolution.

These techniques have been mainly realized in a so-called electronic scan type of ultrasonic apparatus and, in the apparatus of the invention, are put to practical use by properly combining these techniques and by adding other techniques to them, as will be described.

An example of conventional concrete techniques for improving the lateral resolution with respect to the direction of the diagnostic depth follows. In the ordinary ultrasonic diagnosis apparatus, a train of repeating rate pulses having identical wave form, for example, as shown in FIG. 1(a), is set up, and a train of acoustic pulses is emitted on the timing of the rate pulses. An example of echo waves corresponding to the acoustic pulses is shown in FIG. 1(b). Referring to FIG. 2, there are carried out the transmission and the reception of the acoustic pulse beams emitted by, for example, $m_1$ elements (in the first case twelve) of unit transducers UT of an electronic scan probe EP. The grouped emissions of the linearly disposed unit transducers are designated T1a, in accordance with the rate pulse RP1a, of FIG. 1(a).

In the first example of FIG. 2, a focus is set at the relatively long distance point F1a on an imaginary line a1 extending from the probe EP to focus the transmitting and receiving acoustic beams. The determination of the focal point gives the time difference in accordance with particular patterns as to the timing for driving the unit transducers and as to the timing for processing the received echo signal. As the result, the lateral resolution near the focus F1a (the focus position is practically coincident with the position of the center of the beam diameter), namely in the comparatively long distance region, becomes more precise.

Synchronizing the transmission and reception of acoustic pulse beams with the next rate pulse RP1b is carried out with $m_2$ elements (in this case eight) which are less than $m_1$ as shown with T1b of the unit transducers UT. In this case, the focus of the transmitting and receiving beams is set at a point F1b comparatively near the probe EP on an imaginary line a2, set apart a predetermined distance from the line a1. So, the lateral resolution of the image of the portion near the focus F1b, namely the comparatively short distance region, rises.

Moreover, synchronizing with the next rate pulse RP2a, transmission and reception of the acoustic pulse beams are carried again by $m_1$ elements of the unit transducers similar to the T1a, as shown with T2a in FIG. 2. In this case, the acoustic pulse beams focus at a point F2a on an imaginary line a3 apart a further predetermined distance from the line a2 and similar to the focus F1a in distance form the probe EP.

Likewise, synchronizing with the following rate pulse RP2b, transmission and reception of the acoustic pulse beams are carried by $m_2$ elements of the unit transducers UT similar to the T1b as with T2b in FIG. 2. In this case, the acoustic pulse beams focus at a point F2b on an imaginary line a4 set apart another predetermined distance from the line a3 and similar to the focus F1b in distance from the probe EP. After this, the above-mentioned operations are repeated while the driving unit transducer positions and the imaginary line positions are shifted one after another as well-known in the art and shown in U.S. Pat. No. 4,161,122.

The conventional image display system in an ultrasonic diagnosis apparatus is generally composed as shown in FIG. 3, for example, in case of a linear scan. A known display apparatus to display echo images includes, for example, a brightness modulation circuit 2 for conducting to a cathode-ray tube of a display apparatus 1 video signals which include the echo data obtained by the transmission and the reception of the acoustic beams. A blanking control circuit 3 applies to the brightness modulation circuit 2 a blanking control signal to blank unnecessary components of the video signals and the returns of the linear scan in the display apparatus 1. A beam directional sweeping circuit 4 applies to the display apparatus 1 sweeping waves for the linear scan about the acoustic beam direction. A scanning line position signal generator 5 applies to the display apparatus 1 the scanning position-designating signals to designate the scanning position corresponding to each acoustic beam position in the linear scan.

FIG. 1(c) shows the form of the conventional sweeping wave generated from the beam directional sweeping circuit 4, which sweeping wave defines a saw-tooth wave synchronized with the rate pulses as shown in FIG. 1(a).

FIG. 1(d), shows the form of the scanning line position-designating signal generated from the scanning line position signal generator 5. The scanning line designating signal defines the stepping wave the level of which varies with every rate pulse.

FIG. 1(e) shows the form of the blanking control signal generated from the blanking control circuit 3, the blanking in this case being actuated when the blanking control signal is at low level L, and the unblanking signal being actuated when the signal is at high level H. As shown, the blanking control signal is in the unblanking state during the second half of the scanning line when the rate pulse RP1a or RP2a is generated, i.e. for the long distance region, and the blanking control signal is put in the unblanking state at the first half of the scanning line when the rate pulse RP1b or RP2b is generated, i.e., the comparatively short distance region.

Therefore, the display scanning line of each rate pulse in the image display, respectively, corresponds to the axis lines a1, a2 ... of the acoustic beams shown in FIG. 2, and the blanking is actuated as to the short distance region of the display scanning line when the long distance focuses F1a, F2a, etc. are set and the blanking is actuated as to the long distance region of the display scanning line when the short distance focuses F1b, F2b, etc. are set.

Consequently, the echo images having high lateral resolution in both the long distance and the short distance are displayed, and echo images of good quality are obtained over the extensive scope along the acoustic beam direction, namely, the diagnosis depth direction. Apparatus for obtaining these results is taught in U.S. Pat. No. 4,215,584.

However, the conventional system has shortcomings. The echo image display according to the above-described system is executed as shown in FIG. 4. As is apparent, in the conventional case, each scanning line consists of a displayed region UR and an undisplayed region BR because the scanning lines contributing to the display at the short distance region are not displayed during display of the long distance region and the scanning lines contributing to the display at long distance are not displayed during display of the short distance region. As a result, the scanning line density is caused to be substantially reduced by a half. In addition, there is also the problem that, due to the discontinuities in the scanning lines between the short distance region NE and the long distance region FE, confusing and undesirable portions are caused at the border BL between them.

SUMMARY OF THE INVENTION

It is accordingly the object of this invention to provide an ultrasonic imaging apparatus for obtaining an effective pattern of the acoustic wave beam according to the diagnosis distance with good lateral resolution without any decrease of scanning line density and without discontinuities of the scanning lines.

Briefly, this and other objects are achieved in accordance with a first aspect of the invention, by improving ultrasonic imaging apparatus including means for emitting acoustic wave beams of various apertures into a subject, means for receiving the reflected waves corresponding to the beam directions, means for modulating scanning lines corresponding to the reflected beam directions and means for displaying tomographic images of the subject based on a plurality of the modulated scanning lines, wherein the improvement comprises beam control means for directing two acoustic wave beams of substantially different lengths on the same beam direction and display control means for composing the modulated scanning lines of the echo reflections of the two acoustic beams into a single scanning line on the displaying means.

The accompanying drawings, which are incorporated and constitute a part of this specification, illustrate one embodiment of the invention and together with the description, serve to explain the principles of the invention.

BRIEF DESCRIPTION OF THE DRAWING

FIG. 3 is a block diagram illustrating the construction of the image display system in a conventional ultrasonic diagnosis apparatus;

FIG. 4 is a diagram for explaining the display image according to apparatus of FIG. 3;

FIG. 5 is a block diagram illustrating the construction of an embodiment of this invention;

FIG. 9 is a diagram for explaining the display image of the embodiment of FIG. 5.

DESCRIPTION OF THE PREFERRED EMBODIMENTS

Referring to FIG. 5, this embodiment of the invention teaches a system combining a dynamic focus method and a dynamic aperture method relating both to the transmission of sonic beams and the reception of the reflected echo waves.

Figure 8:
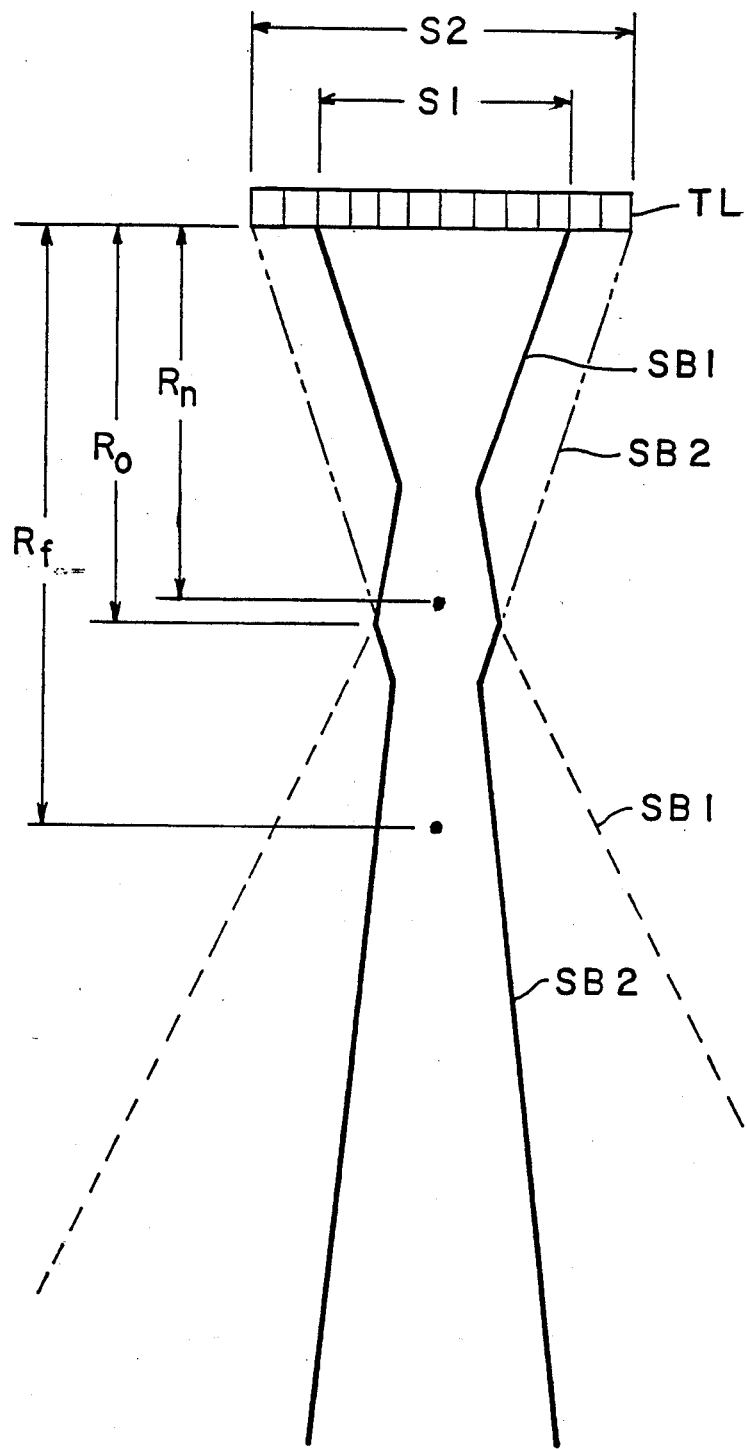
FIG. 8 is a resultant pattern of two acoustic beams of according to the embodiment of FIG. 5.

A probe 11 is provided with a plurality of unit transducers as shown in FIG. 8, desirably arranged for transmission and reception of acoustic waves and a group of pulsers 12 for causing the unit transducers of the probe 11 to oscillate. A first group of delay lines 13 gives a predetermined delay time to trigger pulses generated by pulse oscillator 14 for driving the group of pulsers 12. The delay lines 13 are also used to focus the transmission of the sonic beams as known in the art.

Echo waves reflected from a subject under examination are received and converted into electrical echo signals by the probe 11.

The desired echo signals are detected and amplified by circuit 16 after being given a predetermined time by a second group of delay lines 15. A gain control circuit 17 controls the gain of the amplifying and detecting circuit 16 and a brightness modulation circuit 18 converts the echo signals supplied from the amplifying and detecting circuit 16 to brightness signals for displaying the echo image.

A blanking control circuit 19 actuates blanking signals to the brightness signal output from the brightness modulation circuit 18 for composing the echo signals, as determined previously, to provide display. A beam direction sweeping circuit 20 generates sweeping waves relating to the depth direction, or the acoustic beam direction in case of the echo image display, and a scanning line position signal generator 21 generates the scanning position designating signals corresponding to the beam positions in case of the echo image display. A display apparatus 22 displays the echo images by utilizing each output from the brightness modulation circuit 18, the beam direction sweeping circuit 20 and the scanning line position signal generator 21.

A control apparatus 23 controls each operation of the group of pulsers 12, the groups of delay lines 13 and 15, the pulse oscillator 14, the amplifying and detecting circuit 16, the gain control circuit 17, the blanking control circuit 19, the beam direction sweeping circuit 20 and the scanning line position signal generator 21, as described previously, to govern the operation of the whole system.

Figure 1:
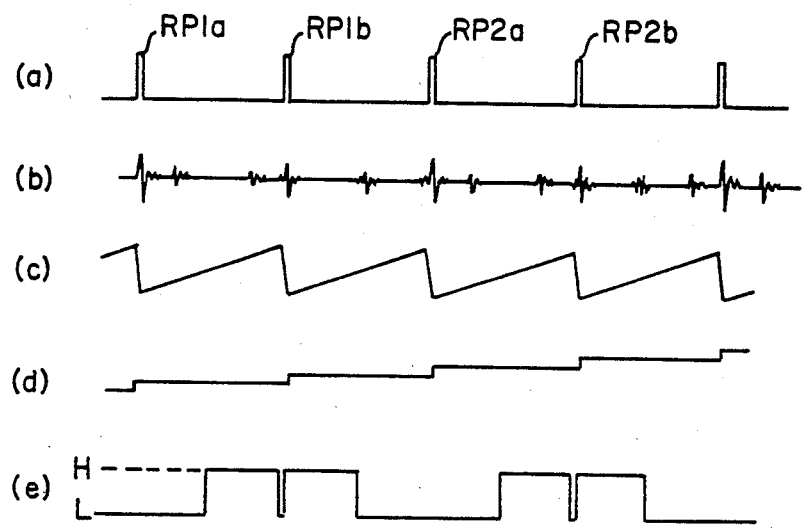
FIGS. 1(a) through (e) are time charts for explaining the operation of a conventional ultrasonic diagnosis apparatus.
Figure 2:
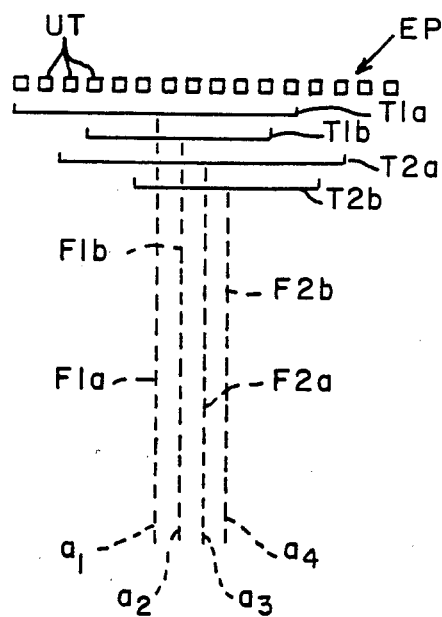
FIG. 2 is a schematic diagram of assistance in explaining the operation of a conventional electronic scan probe.
Figure 6:
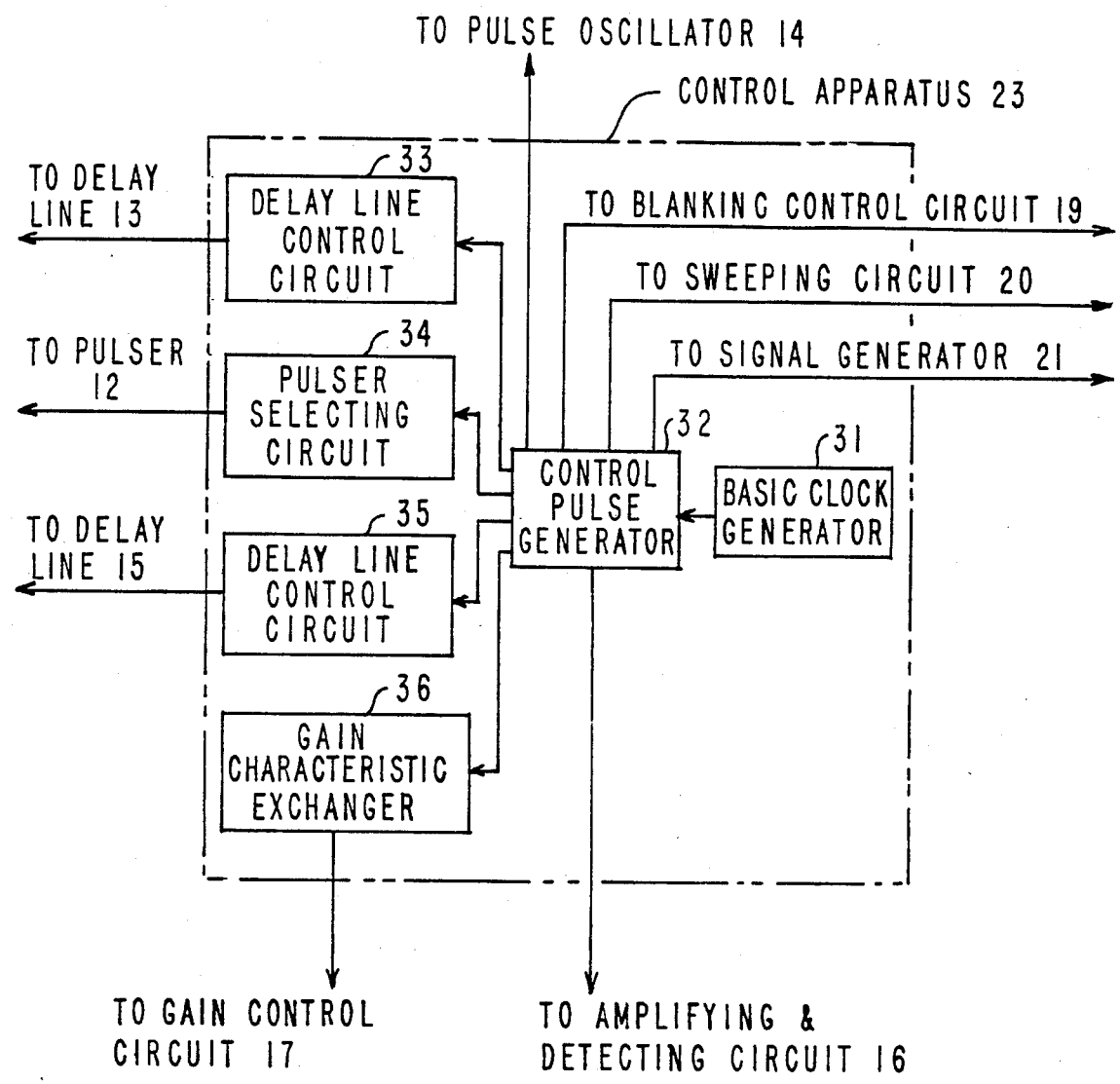
FIG. 6 is a schematic diagram showing portions of the control apparatus of FIG. 5.

The control apparatus 23, as shown in Fig.6, comprises a basic clock generator 31, a control pulse generator 32, a delay line control circuit 35 and a gain characteristic exchanger 36. The control pulse generator 32, comprising timers, frequency dividers and the like, generates square-waves, saw-tooth waves and step waves which are provided with a variety of duty periods according to a clock pulse generated from the clock generator 31. The delay line control circuit 33 selects an analog switch included in the group of delay lines 13 for selecting the value of delay time to perform a scan and focus of acoustic wave beams. The pulser selecting circuit 34 selects the pulser simulaneously actuated of the group of pulsers corresponding to each transducer element of the probe 11. The delay line control circuit 35 operates substantially similar to the delay line control circuit 33 about the group of delay lines 15. The gain characteristic exchanger 36 controls the gain characteristic for every rate pulse.

In operation, trigger pulses are generated by the pulse oscillator 14 in response to pulses of the control apparatus 23 to actuate the group of pulsers 12 through the group of delay lines 13. The unit transducers of the probe 11 are oscillated and acoustic pulses are transmitted from the probe 11.

The acoustic pulses are transmitted out from the probe 11 into the subject and are reflected from a surface in the subject which differs in acoustic impedance, and the subject reflected pulses, namely the echo pulses of the transmission pulses, are returned to the probe 11 to be received by the unit transducers and to be supplied to the group of delay lines 15 as inputs. The echo wave signals received are applied to the group of delay lines 15 and are amplified and detected by the circuit 16 after the predetermined time required to generate echo signals.

Then, the gains of echo signals from the deep portion and the shallow portion in the subject are controlled by the gain control circuit 17 as explained in more detail hereinafter. The echo signals generated by the amplifying and detecting circuit 16 are converted to brightness signals by the brightness modulation circuit 18 and supplied to the display apparatus 22. The display of the brightness output signals from the brightness modulation circuit 18 is controlled by the blanking control circuit 19. In order to display a tomogram of the echo image, beam scanning signals are supplied from the beam direction sweeping circuit 20 and the scanning line position signal generator 21.

Figure 7:
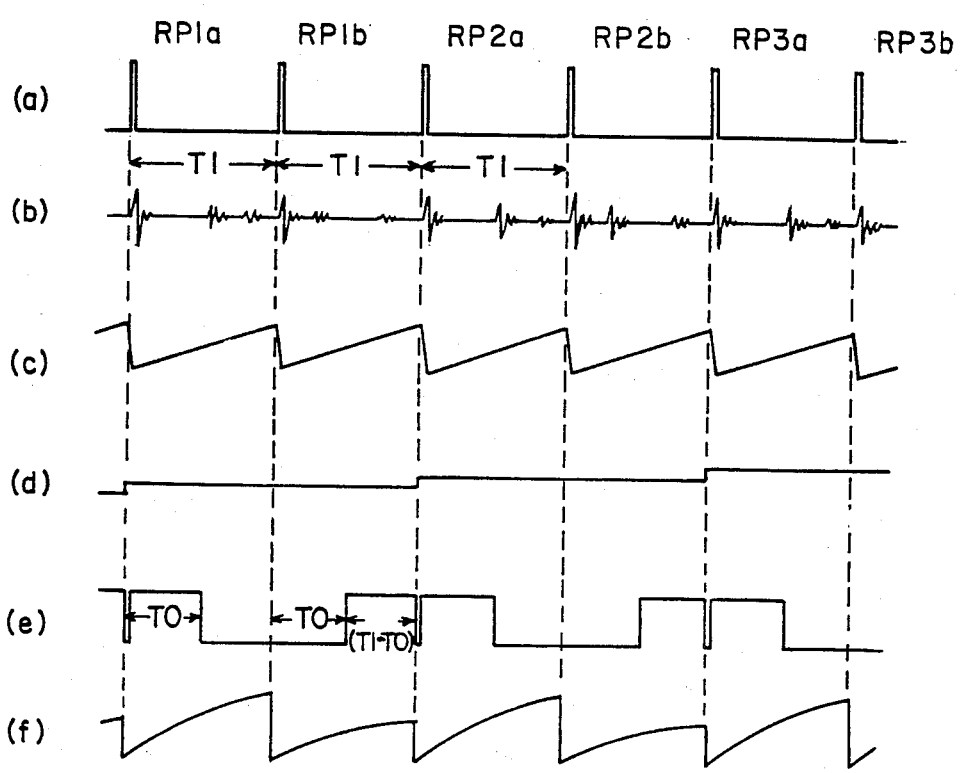
FIGS. 7 (a) through (f) are, timing charts for explaining the operation of the embodiment of FIG. 5.

The timing correlation of the various operations of the circuit arrangement shown in FIG. 5 is indicated in the timing charts of FIG. 7.

FIG. 7(a) shows a wave form of the rate pulses supplied to the probe 11. The rate pulses are constructed as a pulse train which comprises pulses RP1a, RP1b, RP2a, RP2b, . . . having a time interval T1. A wave form of the received echoes corresponding to the rate pulses is shown in FIG. 7(b). In this case, for example, when the rate pulse RP1a is generated, the acoustic wave pulses are emitted by the group of unit transducers (for example, which comprises eight unit transducers) having the apertures S1 within the transducer array TL shown in FIG. 8. The beams are focused by the known controlling method of group of delay lines 13, 15 at transmission and reception, respectively, to define the acoustic beam focus at the comparatively short distance $R_n$ from the transducer array TL. The effective acoustic beams in case of the transmission and the reception corresponding to the rate pulse RP1a are shown with $SB_1$ in FIG. 8.

When the rate pulse RP1b is generated, the acoustic pulses are emitted at same beam position to the one in case of the rate pulse RP1a, i.e. the center of the effective acoustic beam SB1 is identical to that of the beam SB2, by a group of unit transducers which have the aperture $S_2$ (which is more than $S_1$ and comprises, for example, twelve unit transduces) within the transducer array TL shown in FIG. 8. The beams are focused to put the beam focusing distance on $R_f$, ($R_f > R_n$). The effective acoustic beams owing to the rate pulse RP1b are shown with $SB_2$ in FIG. 8.

Next, when the rate plse RP2a is generated, the aperture is $S_1$ and the focusing distance is Rn at the beam position shifted one step, i.e. one lateral width of the unit transducer, from case of the rate pulse RP1a and when the rate pulse RP2b is generated, the aperture is $S_2$ and the focusing distance is $R_f$, then in turn repeating the same operation as just described.

Thus, the display of the tomographic echo images is performed as follows:

FIG. 7(c) shows a wave form of the sweeping wave signals generated from the beam direction sweeping circuit 20 and the sweeping wave signals are synchronized to the rate pulses as shown. FIG. 7(d) shows a wave form of the stepping wave signal generated from the scanning line position signal generator 21 for designating the scanning line position and in this case the signal shifts by predetermined levels every two rate pulses corresponding to the change of beam position.

FIG. 7(e) shows a wave form of the blanking signal generated from the blanking control circuit 19 for composing the echo signals. When the focusing distance is $R_n$ (namely, the short distance), the blanking signals operate as unblanking, only receiving at a period of time T0 of the echo from the short distance acoustic field to display the echo data at the short distance. When however, the focusing distance is $R_f$ (namely, the long distance), the blanking signals operate as unblanking only receiving at a period of time (T1−T0) to display the echo data at the long distance. In this case, the short distance echo receiving time T0 is determined by the following formula on the basis of the distance $R_o$ from the transducer array to the intersecting point focused respectively on the short and long distance:

$T0 = Ro/C$ where:
C is the acoustic wave velocity in the subject. Although the short distance beam SB1 and long distance beam SB2 are each blanked when the other is showing, since they remain on the same scanning line, a simple continuous scanning line is visible on the display to the eye of the observer. Thus, the echo signals on the basis of the acoustic wave beam transmission and reception corresponding to two rate pulses and two lengths of acoustic wave beams are composed into a single scanning line on the display apparatus.

Also, FIG. 7(f) shows a wave form of the gain control signals supplied to the amplifying and detecting circuit 16 from the gain control circuit 17. The gain control signals have respectively different values about the two lengths of acoustic wave beams which respectively differ with an incline of the sensitivity-time control (S.T.C.) corresponding to the depth so as to improve quality of the display in which the sensitivity becomes discontinuity at the intersecting point (the position of distance $R_o$) between the two lengths of acoustic beams owing to the discord in the difference in intensity in the two lengths of acoustic wave.

As a result, the images displayed on the display apparatus 22, as shown in FIG. 9 are a composed image of the short distance acoustic field (time T0) reflecting a good short distance characteristic due to the short distance focus and the small aperture, and the long distance acoustic field (the period of time T1−T0) reflecting a good long distance characteristic due to the long distance focus and the large aperture. Thus, good lateral resolution for the short distance and the long distance are shown extending the whole imaging distance on the display. Although the blanking time exists in the process of composing each scanning line, there is no visual distinction of discontinuity and there is no observation problem in practice even though a time delay for image-defining actually exists. Since the composing is performed wit h each scanning line, there is no decrease of the scanning line density and there is no observed discontinuity.

Moreover, the invention can be carried out in a variety of modifications in the scope of the invention without limiting it to the embodiment as described. Although, ithas been found that a change in focus to accommodate an increase in depth is best achieved by increasing the number of ultrasonic transducers to be driven, it is known that the focus distance may be changed while using the same number of actuated transducers and, indeed, the focus distance may be changed with the number of transducers inversely related to the depth. Moreover, ultrasonic imaging apparatus may be constructed wherein the number of transducers is changed with a fixed focus distance. Further, showing the timing charts corresponding to ones in FIG. 7(a) through (f) in FIG. 10 (a) through (f), the period of time (T1−T0) within ones corresponding to the rate pulses $RP_{1a}$, $RP_{2a}$, ... may be eliminated.

Figure 10:
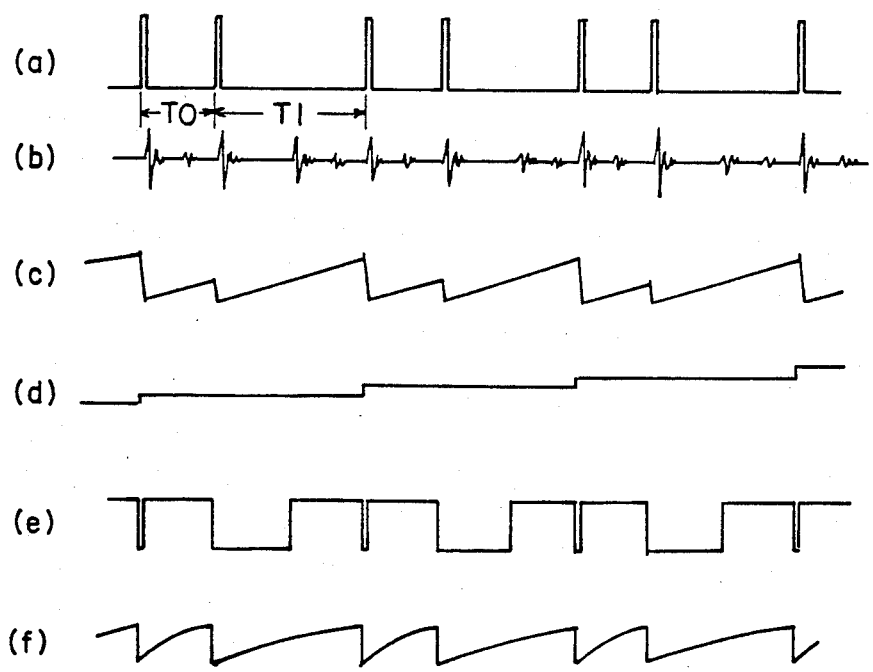
FIG. 10 (a) through (f) are time charts for explaining an alternate embodiment of the invention.

As shown in FIG. 10, the rate pulses $RP1a$, $RP2a$, ... are emitted for a period T0 only, and the rate pulses $RP1b$, $RP2b$, ..., having the longer focal distance, are emitted for a longer period of time T1. As further shown by FIG. 10(e) the beams $RP1a$, $RP12a$, ... with the shorter focusing distance are unblanked, and the beams $RP1b$, $RP2b$, ... are blanked during the period T0 but are unblanked during the period T1−T0.

Furthermore, three or more acoustic beams may be composed for forming a scanning line according to the principles of the invention.

Moreover, the invention may apply not only to linear scan but also to other scan systems such as sector scan, radial scan and the like.

As described above, in accordance with the invention, ultrasonic imaging apparatus can be provided wherein good lateral resolution can be obtained without decrease of scanning line density and without observable discontinuity of the scanning lines.

What we claim is:

1. An apparatus for ultrasonically imaging a section of an object under investigation, said apparatus comprising:
    (a) an array of ultrasonic transducer elements for transmitting ultrasonic beams of various focal distances into said section of said object and for receiving reflections of transmittal beams;
    (b) pulse transmitting means for energizing said transducer elements to transmit said ultrasonic beams into said section;
    (c) means, coupled to said pulse transmitting means, for focusing selected ones of said ultrasonic beams into a near range zone and different selected ones of said beams into a far range zone within said section by utilizing more of said transducer elements for said far zone focusing than for said near zone focusing;
    (d) means, coupled to said array of ultrasonic transducer elements, for detecting and processing signals corresponding to ultrsonic beam reflections received by said transducer elements from said near and far range zones of said section;
    (e) means, coupled to said detecting and processing means, for imparting a first time-varying gain control to the detected signals corresponding to reflected beams from said near range zone and for imparting a second time-varying gain control to the detected signals corresponding to reflected beams from said far range zones, said first time-varying gain control having a faster time rate of change of gain than said second time-varying gain control, said gain control means including means for adjusting said gain controls to accommodate variations in the focus of said selected beams; and
    (f) means, coupled to said detecting and processing means, for displaying said signals corresponding to said received ultrasonic beams after said time-varying gain control has been imparted to said signals.

2. The apparatus in claim 1 wherein said beam focusing means includes a delay circuit.

3. The apparatus in claim 1 wherein said detecting and processing means includes a control circuit, an amplifying and detecting circuit, a brightness modulation circuit and a blanking control circuit.

4. The apparatus in claim 3 wherein said control circuit includes:
    a clock generator;
    a control pulse generator coupled to said clock generator for generating control pulses for said blanking control circuit, and said amplifying and detecting circuit;
    focus control circuitry for generating control pulses for said beam focusing means; and
    a gain characteristic exchanger for generating control pulses for said gain imparting means.

5. The apparatus in claim 1 wherein said focusing means causes the ultrasonic beams of various focusing distances have a common focal axis.

6. The apparatus of claim 5 wherein the gain imparting means produces gains which increase with time.

7. The apparatus in claim 1 wherein said array is linear.

* * * * *